(12) United States Patent
Larson

(10) Patent No.: US 6,505,061 B2
(45) Date of Patent: Jan. 7, 2003

(54) PULSE OXIMETRY SENSOR WITH IMPROVED APPENDAGE CUSHION

(75) Inventor: Eric Russell Larson, Boulder, CO (US)

(73) Assignee: Datex-Ohmeda, Inc., Madison, WI (US)

(*) Notice: Subject to any disclaimer, the term of this patent is extended or adjusted under 35 U.S.C. 154(b) by 0 days.

(21) Appl. No.: 09/839,533

(22) Filed: Apr. 20, 2001

(65) Prior Publication Data
US 2002/0156353 A1 Oct. 24, 2002

(51) Int. Cl.7 ................................................ A61B 5/00
(52) U.S. Cl. ....................... 600/323; 600/344; 600/322
(58) Field of Search ............................... 600/309–310, 600/322–324, 344

(56) References Cited

U.S. PATENT DOCUMENTS

| | | |
|---|---|---|
| 4,685,464 A | 8/1987 | Goldberger et al. |
| 4,722,120 A * | 2/1988 | Lu ............................... 24/489 |
| 4,830,014 A | 5/1989 | Goodman et al. |
| 4,913,150 A * | 4/1990 | Cheung et al. ............. 600/323 |
| 5,247,931 A | 9/1993 | Norwood |
| 5,279,295 A | 1/1994 | Martens et al. |
| 5,313,940 A | 5/1994 | Fuse et al. |
| 5,339,810 A | 8/1994 | Ivers et al. |
| 5,438,986 A | 8/1995 | Disch et al. |
| 5,511,546 A | 4/1996 | Hon |
| 5,676,139 A | 10/1997 | Goldberger et al. |
| 5,810,724 A | 9/1998 | Gronvall ..................... 600/323 |
| 5,817,010 A | 10/1998 | Hibl ............................ 600/344 |
| 5,829,439 A | 11/1998 | Yokosawa et al. |
| 5,851,178 A | 12/1998 | Aronow ...................... 600/323 |
| 5,910,108 A | 6/1999 | Solenberger ................ 600/310 |
| 5,913,819 A | 6/1999 | Taylor et al. ................ 600/323 |
| 6,055,447 A * | 4/2000 | Weil et al. ................... 600/353 |
| 6,112,107 A | 8/2000 | Hannula ...................... 600/310 |
| 6,151,516 A | 11/2000 | Kiani-Azarbayjany et al. .. 600/322 |
| 6,285,895 B1 * | 9/2001 | Ristolainen et al. ......... 600/323 |
| 6,321,100 B1 * | 11/2001 | Parker et al. ................ 600/344 |

* cited by examiner

Primary Examiner—Eric F. Winakur
Assistant Examiner—Matthew Kremer
(74) Attorney, Agent, or Firm—Marsh Fischmann & Breyfogle LLP

(57) ABSTRACT

The invention is directed to reusable, clip-type oximetry sensors that comprise opposing top and bottom members. In one aspect, the sensor includes a resilient spring member interposed between the top and bottom members to provide a closing force, wherein the resilient spring member comprises tensile and compressive portions. That is, upon positioning a patient appendage in the sensor different portions of the resilient spring member are in tension and in compression so as to combinatively provide an enhanced closing force utilized to secure the patient appendage between the top and bottom members. The resilient spring member may be of a molded, monolithic construction, comprising an elastomeric material. In another aspect, the inventive sensor includes cushions interconnected to the top and bottom members via snap-fit engagement. The snap-fit engagement may be provided by a plurality of interconnecting member pairs (e.g., projections and mating recesses), wherein the connection axes of the members comprising each pair are transversely disposed to yield enhanced interconnection via two-dimensional restraint between the cushions assemblies and top and bottom members.

28 Claims, 5 Drawing Sheets

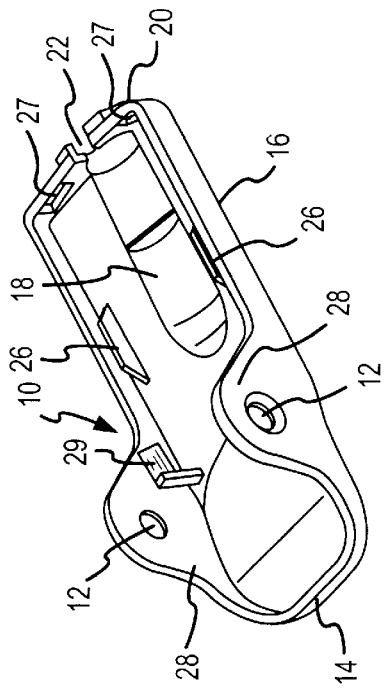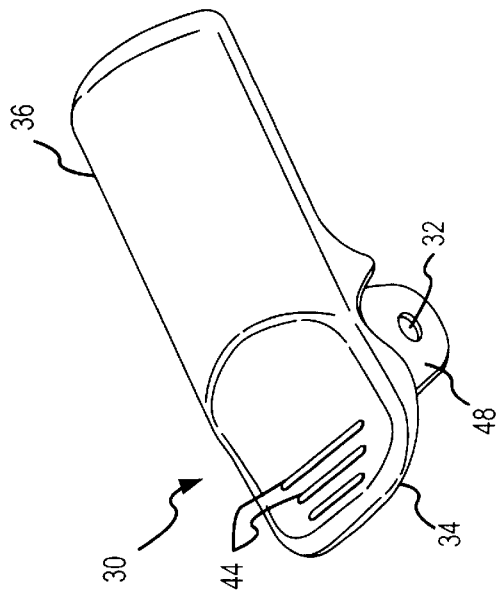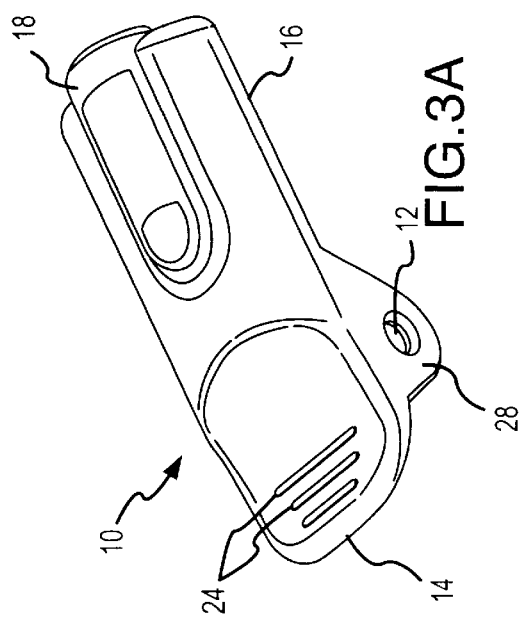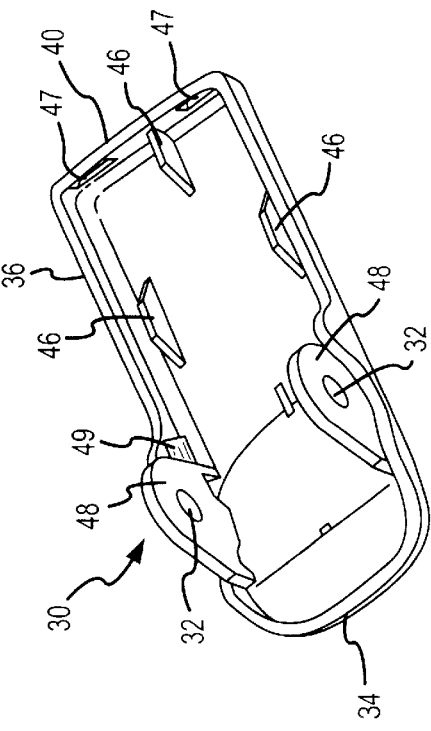

US 6,505,061 B2

PULSE OXIMETRY SENSOR WITH IMPROVED APPENDAGE CUSHION

FIELD OF THE INVENTION

The present invention is generally directed to photoplethysmographic measurement instruments, and more specifically to clip-type pulse oximetry sensors which attach to patient appendages.

BACKGROUND OF THE INVENTION

A common technique used to monitor blood oxygen levels is pulse oximetry. In this regard, it is known that the light transmissivity and color of blood is a function of the oxygen saturation of the heme in the blood's hemoglobin. For example, heme that is saturated with oxygen appears bright red because saturated heme is relatively permeable to red light. In contrast, heme that is deoxygenated appears dark and bluish as it is less permeable to red light. A pulse oximeter system measures the oxygen content of arterial blood by first illuminating the blood with red and infrared radiation and determining the corresponding amounts of red and infrared radiation that are absorbed by the heme in the blood. In turn, such light absorption amounts may be employed in conjunction with known calibration information to determine blood oxygen levels.

Pulse oximetry sensors generally include one or more light emitters, a detector, and a means for holding the emitter(s) and detector in contact with a patient's tissue so that an optical path is established through the tissue. There are various means for holding the emitter(s)/detector in contact to a patient's tissue; however, two common types are flexible and clip-type sensors. Flexible sensors may simply comprise an adhesive strip onto which the emitter(s)/detector are mounted for placement about a patient appendage. Clip-type sensors typically include two hingedly connected housings onto which the emitter(s) and detector are mounted. Generally, clip-type sensors are releasably attached to a patient's appendage (e.g., finger, ear lobe or the nasal septum) so that the appendage is isolated between the two housings.

Both mentioned sensor types present advantages and disadvantages. In particular, clip-type sensors may be advantageously reused on different patients and are relatively easy to attach to and remove from a patient tissue site. Further, the present inventor has recognized the desirability of providing a reusable sensor which securely attaches to a patient's appendage while reducing any interference with blood circulation, which is resistant to contamination, which yields reduced relative appendage movement, which is durable and which is configured for ease of assembly.

SUMMARY OF THE INVENTION

In view of the foregoing, a primary object of the present invention is to provide a reusable oximeter sensor which securely and reliably attaches to a patient's appendage while reducing any arterial blood flow interference.

Another objective of the present invention is to provide a reusable oximeter sensor that inhibits contaminant infiltration.

A further object of the present invention is to provide a reusable oximeter sensor which reduces relative movement of an inserted appendage.

An additional object of the present invention is to provide a reusable oximeter sensor having enhanced durability.

Yet another objective of the present invention is to provide a reusable pulse oximetry sensor which is relatively easy to assemble.

One or more of the above objectives and additional advantages are realized by the present invention. In one aspect, a clip-type pulse oximetry sensor is provided which comprises top and bottom members disposed in opposing and hinged relation, and a spring member interposed therebetween. More particularly, a resilient spring member may be located between the sensor's top and bottom members near a rearward end of the members (e.g., an end opposite to that which securably receives a patient appendage). The resilient spring member acts to provide the force required to close and thereby hold the forward ends of the top and bottom members on a patient's inserted appendage. Of note, the closing force may be provided by a combination of tensile and compressive portions integrated into the spring member. That is, when the sensor is secured upon a patient appendage a portion of the resilient hinge member is actuated to be tensioned and another portion is actuated to be compressed. Attempting to return to their non-deformed static condition, the tensile and compressive portions combinatively exert an enhanced closing force to reliably hold the sensor to the inserted appendage.

Preferably, contact surfaces of the spring member directly engage both the top and bottom members when the sensor is assembled, thereby facilitating force transfer therebetween. The contact surfaces may comprise wings which extend rearwardly at the top and bottom of the spring member. Relatedly, rearward ends of the top and bottom members may be rimmed and/or otherwise configured to provide conformal seats for flushly receiving the spring member wings. When compressive forces are applied to the rearward ends of the top and bottom members (e.g., via hand manipulation) the spring member wings are forced towards one another, compressing a rearward-facing portion of the spring member while tensioning a forward-facing portion of the spring member. Correspondingly, the forward ends of the top and bottom members will open to accommodate patient appendage insertion/positioning therebetween. When the compressive forces are released, the tensile and compressive portions of the spring member co-act to provide the above-noted closing force.

A rearward-facing side of the spring member (e.g., extending between the above-noted wings) is preferably defined by a continuous surface. For example, in a winged embodiment having a U-shaped profile, the rearward side of the spring member may comprise a concave, semi-cylindrical surface that extends between the top and bottom members across the width of the sensor to completely close the rear-end of the sensor. As may be appreciated, the provision of a continuous rearward surface on the spring member reduces contaminate infiltration into the sensor.

Of note, the spring member may be advantageously defined as a one-piece unit. More particularly, the resilient spring member may have an integral, monolithic structure. To provide such a structure, the spring member may advantageously comprise a molded polymeric material.

In the latter regard, and more generally, the resilient spring member preferably comprises an elastomeric material. By way of example only, the spring member may a material selected from a group consisting of thermoplastic elastomers, liquid silicone rubbers, polyolefin elastomers, thermoplastic rubbers urethanes and natural rubbers. The utilization of an elastomeric spring member facilitates the realization of a range of spring constants for different applications of the inventive sensor. As such, the same basic design/componentry of the inventive sensor may be employed for a number of different patient applications entailing different desired clamping forces for patient appendage securement. That is, only the specific elastomer utilized in the spring members needs to vary from sensor to sensor. For example, a large-finger patient sensor may comprise a spring member having a different modulus of elasticity than that of another spring member utilized in a small finger patient sensor.

Preferably, the spring member may comprise one or more openings to accommodate hinged interconnection of the top and bottom members and/or to allow for the routing of electrical wiring between the top and bottom members. More particularly, the spring member may comprise an opening extending laterally therethrough from side to side to accommodate a hinge pin that hingedly interconnects the top and bottom members. In this embodiment, the hinge pin acts as a fulcrum or hinge axis for the top and bottom members. Additionally, the hinge pin functionally separates the above-noted tensile and compressive portions of the hinge member. For example, when the sensor is opened (e.g. to accommodate insertion or after insertion of a patient appendage), the portion of the spring member in front of the hinge pin is pulled in tension while the portion rearward the pin is compressed.

The spring member may also include a slot that extends from the top of the spring member to the bottom thereof to provide a passageway to route electrical wiring for emitter and/or detector componentry carried by the top and bottom members. Preferably, the slot is located on a forward-facing side of the spring member. In one embodiment, the slot is located on the spring member's vertical centerline and extends from the front of the spring member and in to the lateral opening of the spring member. This arrangement effectively divides the above-noted tensile portion into two separated sides. During assembly electrical wiring for emitter and/or detector componentry may be routed through the slot and retained behind the hinge pin, thereby isolating and protecting the wires.

The lateral opening through the resilient spring member may also advantageously include a keyway slot. Correspondingly, the hinge pin may include an outwardly projecting key member slidably positionable in the keyway slot. Such an arrangement orients the hinge pin about a symmetry plane of the spring member. During actuation of the spring member, the slot allows the hinge pin to float with the symmetry plane, thereby equalizing the stress within the spring member. In turn, the actuation life of the spring member may be enhanced.

According to another aspect of the present invention, a clip-type pulse oximeter sensor is disclosed that comprises opposing and hingedly connected top and bottom members, and a cushion interconnected to one of the top and bottom members. Preferably, cushions are interconnected to each of the top and bottom members.

Each cushion may comprise a frame and a pliable member supported about a polygonal area by the frame. In turn, an optical window (e.g., a plastic lens) may be supported about its periphery within said polygonal area by the pliable member. Generally, each cushion may be interconnected to a top or bottom member, wherein the pliable member is free to flexibly conform to a patient's appendage and thereby locate the optical window in intimate relation to the patient appendage. Relatedly, one or more light emitter(s) or light detector(s) may be located adjacent to, and preferably connected to, each optical window.

Of note, the pliable member may comprise an elastomeric material (e.g., a synthetic rubber) that is over-molded onto the frame. In turn, the frame may comprise a molded polymeric material (e.g., a glass-filled polymer that bonds well with an elastomeric pliable member). Such an arrangement enhances the pliable member/frame interconnection and facilitates effective load transfer therebetween.

Of note, the cushions may be advantageously attached to the top and bottom members using snap-fit means. The snap-fit means may include a plurality of interconnecting member sets to attach each given cushion to a top or bottom member. Each of the interconnecting member sets may comprise a projection and a mating recess. In turn, each of the cushions and top and bottom members may comprise at least one projection and at least one mating recess to facilitate secured interconnection therebetween. Further, the recesses may be configured so as to restrict movement of a corresponding projection in at least two dimensions.

As may be appreciated, the projections and recesses may be integrated into the above-noted cushion frames and interfacing top and bottom members. In such arrangements, the frames and each of the top and bottom members may advantageously comprise at least one projection and at least one mating recess. Preferably, different ones of a plurality of interconnecting member sets may be located on the opposing sides of the sensor and on the forward side of the sensor.

As noted, a plurality interconnecting member sets may be advantageously utilized. Preferably, these interconnecting member sets are oriented so that their respective interconnection axes are transverse to one another. By transversely orienting the connection axes, a given cushion may be securely locked into a top/bottom member to restrict relative movement in three dimensions. For example, use of interconnecting members sets on at least two sides of a polygonal (e.g. rectangular) cushion frame and interfacing bottom/top member facilitates a secure interconnection both laterally and longitudinally, as well as in the depth profile. Such arrangements effectively restrict relative movement between sensor componentry upon patient movements during use.

Additional aspects advantages of the present invention will become apparent upon consideration of the further description that follows.

DESCRIPTION OF THE DRAWINGS

FIGS. 3A and 3B are perspective views of an outward-facing surface and an inward-facing surface, respectively, of a top member of the embodiment of FIG. 1.

FIGS. 4A and 4B are perspective views of inward-facing and outward-facing surfaces, respectively, of a bottom member of the embodiment of FIG. 1.

DETAILED DESCRIPTION

Figure 1:
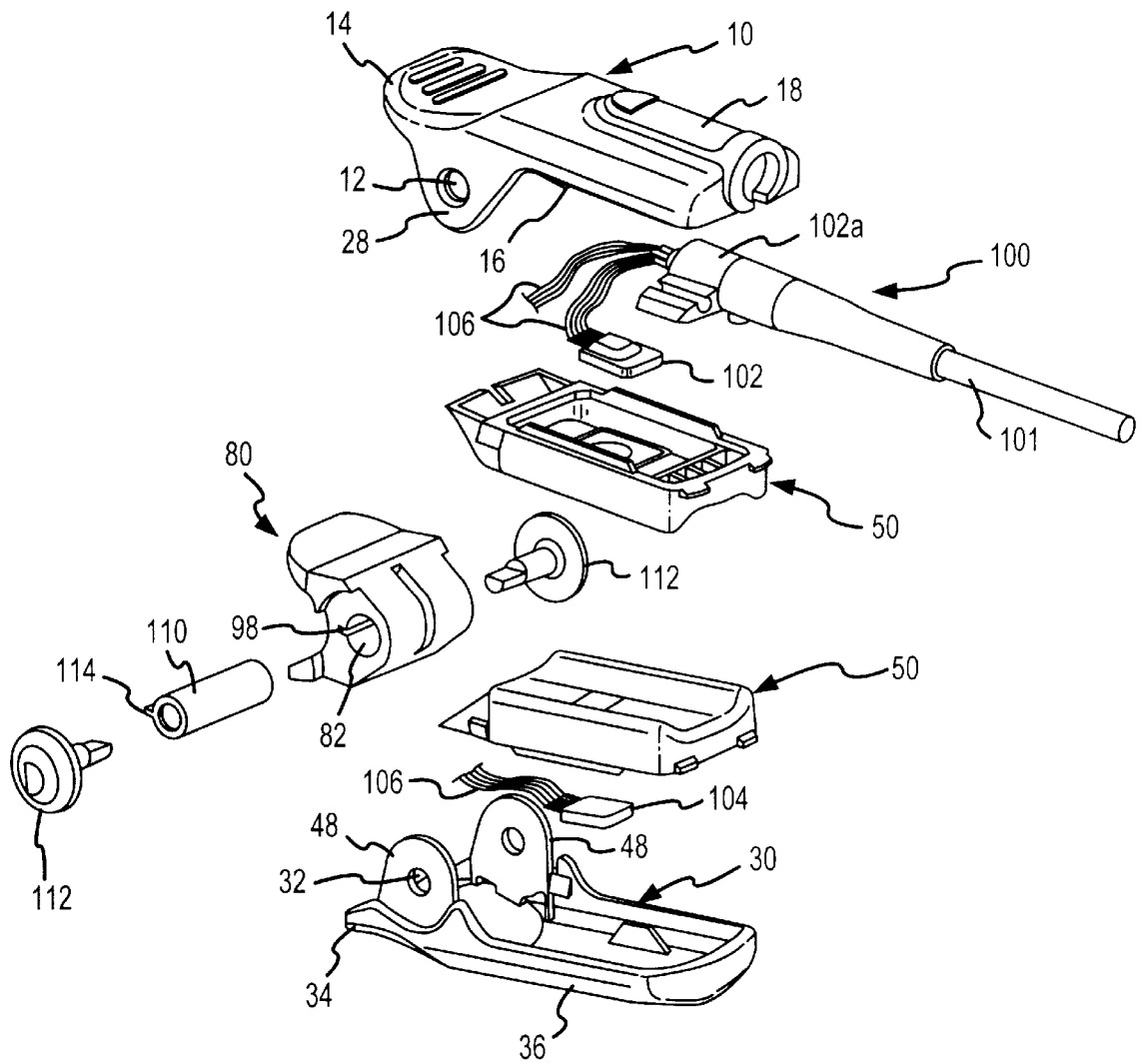
FIG. 1 is an exploded view of one embodiment of the present invention.
Figure 2:
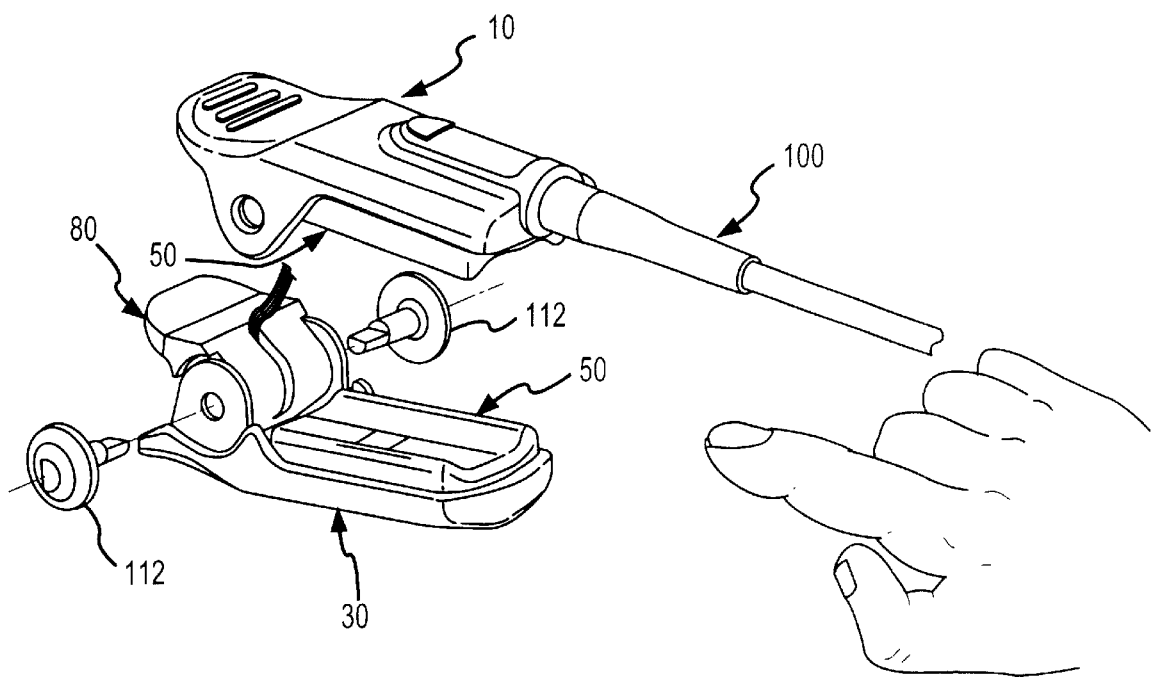
FIG. 2 is an exploded view of the embodiment of FIG. 1 in a partially assembled form.
Figure 5A:
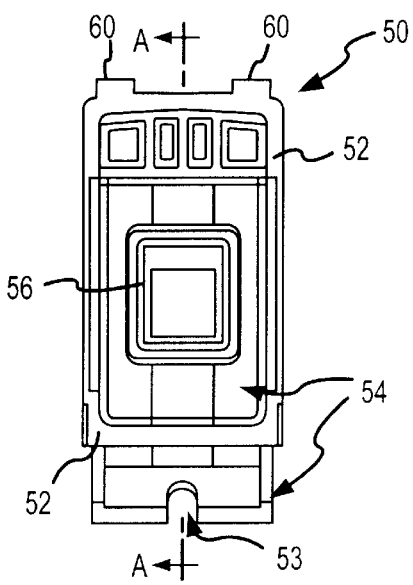
FIG. 5A is a plan view of an internal side of a cushion assembly of the embodiment of FIG. 1.
Figure 5C:
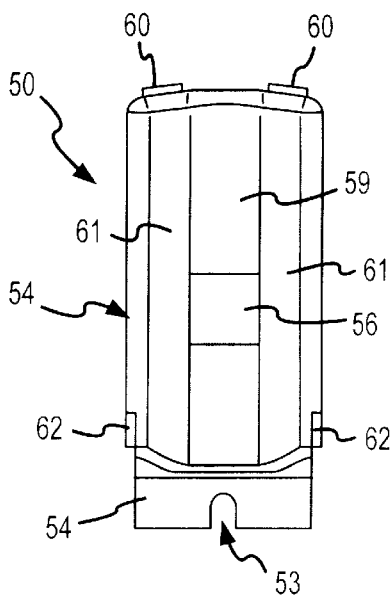
FIG. 5C is a plan view of an external side of the cushion assembly shown in FIG. 5A.
Figure 5B:
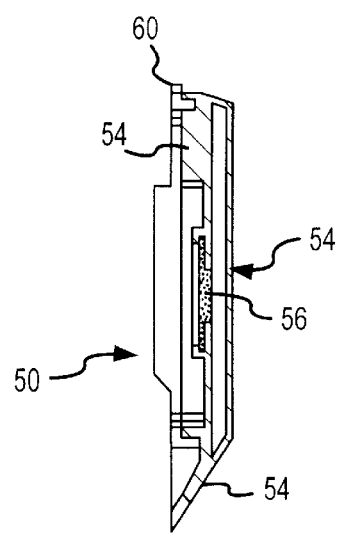
FIG. 5B is a cross sectional view of the cushion assembly shown in FIG. 5A taken along line AA thereof.
Figure 5D:
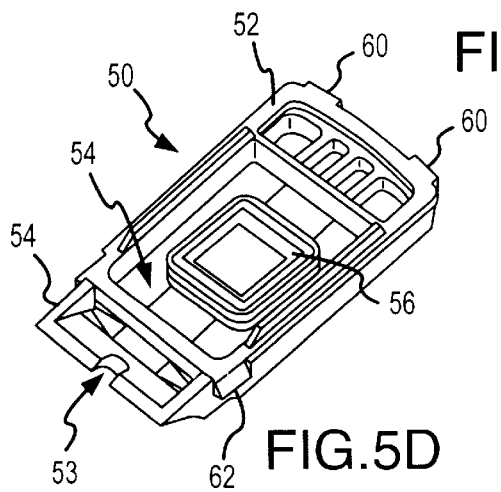
FIG. 5D is a perspective view of the internal side of the cushion assembly shown in FIG. 5A.
Figure 5E:
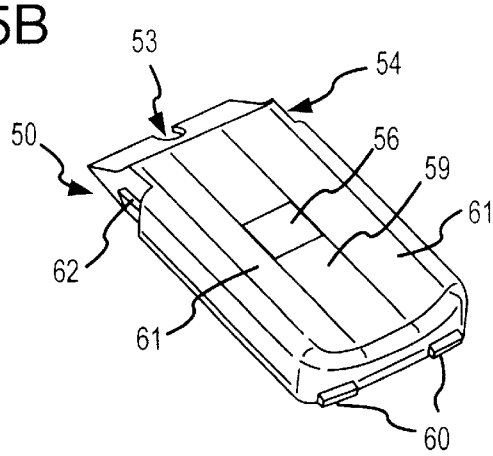
FIG. 5E is a perspective view of the external side of the cushion assembly shown in FIG. 5C.

FIGS. 1 and 2 show exploded views of a pulse oximeter sensor embodiment of the invention comprising a top member 10, a bottom member 30, two corresponding cushion assemblies 50, and a resilient spring member 80. Once assembled, the top and bottom members 10, 30, and the corresponding cushion assemblies 50 interface along their respective longitudinal axes, with the two cushion assemblies 50 directly opposed. In this regard, the sensor's longitudinal axis may be aligned with the insertion direction of a patient appendage, in this case a patient's finger or toe.

Near the rearward end of the sensor, the top and bottom members 10, 30 are interconnected by a cylindrical hinge pin 110 that passes through an opening 82 in the resilient spring member 80 and receives hinge buttons 112 inserted through openings 12, 32 in side stirrups 28, 48 of the top and bottom members 10, 30. The center axis of hinge pin 110 may be oriented perpendicular to the longitudinal axis of the sensor.

The sensor opens by pressing rearward ends 14, 34 of the top and bottom members 10, 30 together. This deforms the spring member 80 and separates forward ends 16, 36 of the top and bottom members 10, 30. Such separation allows insertion of a patient's finger for positioning between the cushion assemblies 50. Once the forces applied to top and bottom members 10, 30 are released, the hinge member 80 will close the forward ends 16, 36 and thereby secure the sensor on the inserted appendage.

As shown, the sensor may further include an illumination/detection assembly 100 comprising a signal connection cable 101, and least one light emitter 102 and light detector 104 interconnected via wiring 106 to the signal connection cable 101. As will be appreciated, signal connection cable 102 may be interconnected to a pulse oximeter monitor that provides drive signals to effect light emission by light emitter(s) 102 and that processes detection signals output by detector(s) 104 to provide blood oxygenation levels.

Figure 6A:
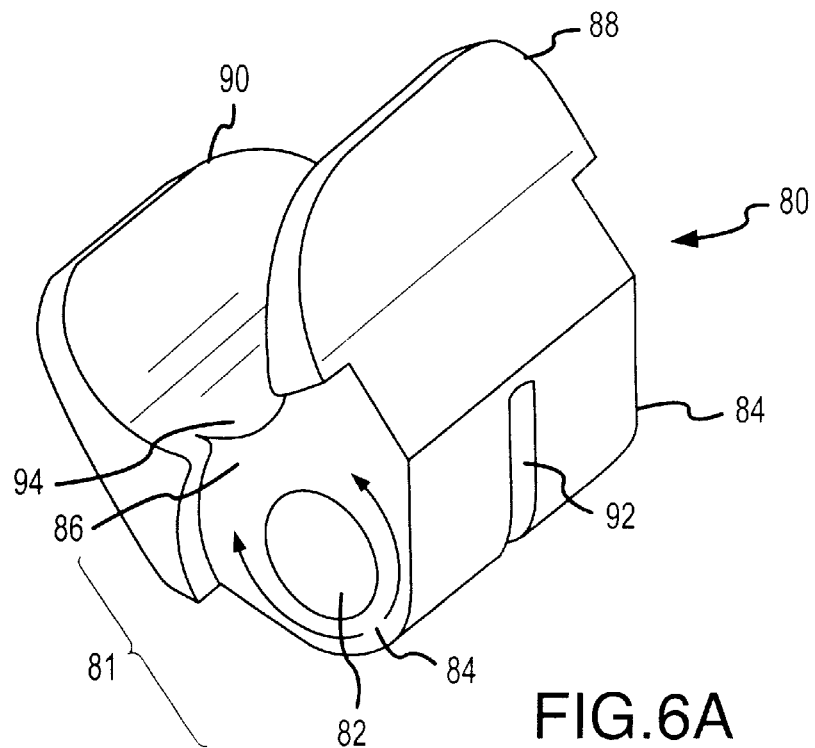
FIGS. 6A and 6B are two perspective views of a resilient spring member of the embodiment of FIG. 1.
Figure 6B:
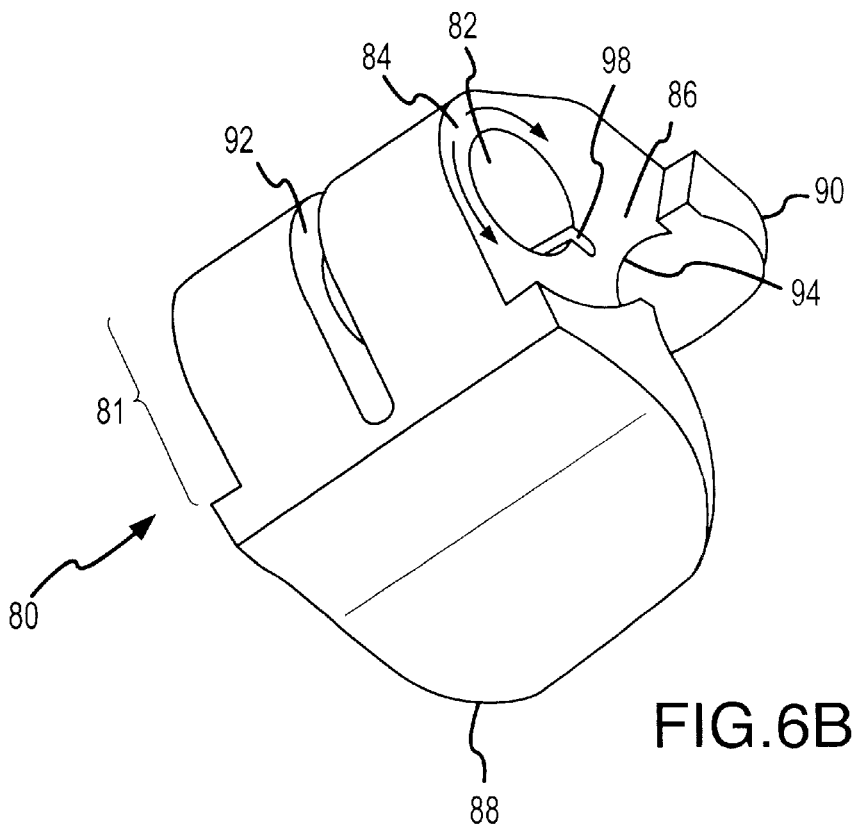

Referring now to FIGS. 6A and 6B with FIGS. 1 and 2, it can be seen that resilient spring member 80 may be a one-piece, monolithic unit that extends between the top and bottom members 10, 30 upon assembly. In this regard, the illustrated spring member 80 comprises several unique features. For example, spring member 80 may comprise a main body 81 defined by a combination of tensile and compressive portions 84 and 86, respectively, used to produce the sensor's closing force. Additionally, spring member 80 may comprise an elastomeric material that is molded to yield a desired configuration and modulus of elasticity. By way of example, the elastomeric material may be selected from a group consisting of liquid silicon rubber (e.g., Silastic offered by Dow Corning), thermoplastic elastomers, polyolefin elastomers, thermoplastic rubbers, natural rubbers, and urethanes. With a liquid silicon material, spring member 80 can advantageously yield durometric shore readings of 25 to 50.

Spring member 80 may further include top and bottom wings 88, 90 which are configured to flushly engage and fit within the rearward ends 14, 34 of the top and bottom members 10, 30. Additionally, spring member 80 may include a substantially continuous surface 94 that extends across the width of the sensor between the wings 88, 90. In the illustrated embodiment, surface 94 is of a semi-cylindrical, concave configuration. Unlike a wire spring which may necessarily leave open space for wire movement, the continuous surface 94 of spring member 80 closes off the reward end of the sensor to reduce particulate infiltration into the sensor.

As noted above, the spring member 80 also includes an opening 82 extending laterally therethrough to receive hinge pin 100. In the illustrated embodiment, the tensile portion 84 of the spring member 80 is located on the forward side of the hinge pin opening 82. The compressive portion 86 is located on the rearward side of the hinge pin opening 82. A keyway slot 98 may be provided with the opening 82 to slidably receive a projecting key 114 on the hinge pin 110. The spring member 80 also contains a slot 92 for the passage of the wiring 106 that extends between detector(s) 104 and cable 101. The slot 92 may be located on the centerline of the hinge member 80 and on the forward side thereof to define two tensile subportions (e.g., one on each side of the slot 92).

Referring now to FIGS. 3A, 3B and FIGS. 4A, 4B, a further description of the top and bottom members 10, 30 will be provided. As shown in FIGS. 3A and 3B, top member 10 includes a protruding, semi-cylindrical portion 18 sized to receive and locate a cylindrical stand-off end 101a of cable 101 (see also FIGS. 1 and 2). Relatedly, an end flange 20 is provided with a circular opening 22 in the forward end 16 of the top member 10 to restrainably engage the stand-off end 101a of cable 101.

The rearward ends 14, 34 of the top and bottom members 10, 30 are each rimmed about their periphery to seatably receive wings 88, 90 of the spring member 80. Further, the rearward end 14, 34 are curved and flair outwardly from the sensor's longitudinal axis at a slight angle. This curved configuration is also presented by the wings 88, 90 and main body 81 of the resilient spring member 80 (See FIGS. 6A and 6B). As may be appreciated, such curved configuration accommodates hand manipulation by a user, including the application of compression forces to apply/remove the sensor from a patient's finger. Further in this regard, one or more ridges 24, 44, may be provided to further facilitate hand manipulation.

As noted above, top and bottom members 10, 30 also include side stirrups 28, 48 with corresponding openings 12, 32 for accommodating hinged interconnection of the top and bottom members 10, 30. Further in this regard, the side stirrups 48 on the bottom member 30 are located nearer the sensor longitudinal axis than side stirrups 28 on the top member 10. Further, the sides of the bottom member 30 are configured to present a contoured ledge that opposes the side stirrups 28 of the top member 10 upon assembly.

With particular reference to FIGS. 3B and 4A, it can be seen that internal, downward-facing and upward-facing surfaces of the top and bottom members 10, 30, include projecting fin members 26, 46 for locating cushion assemblies 50. Additionally, forward end flanges 20, 40 of the top and bottom members 10, 30 include recesses 27, 47 for use in receiving cushion assemblies 50 in a snap-fit engagement. For such purposes, ramped, or wedge-shaped, projections 29, 49 are also provided along the internal sidewalls of the top and bottom members 10, 30.

As may be appreciated, the top and bottom members 10, 30 may be constructed as one-piece units. For example, the top and bottom members 10, 30 may be of a molded plastic construction.

FIGS. 5A–5E illustrate an exemplary one of the cushion assemblies 50. As shown, each cushion assembly 50 comprises a rigid frame 52 (e.g., of molded construction) that supports a pliable member 54 about the periphery of the pliable member 54. In turn, the pliable member 54 supports an optical window 56 (e.g., a clear polycarbonate lens) about the periphery of the optical window 56, thereby effectively defining a gimbel support arrangement. In this regard, it may be noted that the frame 50 has no internal cross-support within a defined region adjacent to the optical window 56, thus allowing pliable member 54 to flexibly deform when a force is applied to the pliable member 54. Such an arrangement facilitates conformal positioning of the optical window 56 adjacent to a patient's finger during use.

By way of primary example, the pliable member 54 may be over-molded on to the frame 52 and optical window 56. For such purposes, the pliable member 54 may comprise a polymeric material, e.g., a thermoplastic elastomer or liquid silicon. In particular, pliable member 54 may comprise a synthetic elastomer such as Krayton or Versaflex. As may be appreciated, the use of such a material also yields a tactile surface that facilitates finger securement. Relatedly, the frame 52 may also comprise a polymeric material, e.g., a 10% glass fiber ABS (acrylonitrile-butadiene-styrene) material. The use of the noted materials and molded/over molding construction yields a highly durable interface between the pliable members 54 and frames 52.

The forward and rearward ends of the frames 52 may be configured to present concave, curved support surfaces. In turn, the pliable member 54 may be provided to have a central flat portion 58 that runs the length of the cushion assembly 50 and is equal in width to the optical window 56. Additionally, the pliable member 50 has two arcuate side portions 60 which extend parallel with the longitudinal axis of the sensor on each side of the central portion 58. The central and side portions 58, 60 collectively define a concave, semi-cylindrical surface that facilitates conformal patient appendage interface.

To facilitate snap-fit engagement with the top and bottom members 10, 30, the frame 52 of each cushion assembly 50 includes two tabs 60 located on the forward edge thereof. These tabs 60 extend parallel with and are located on opposing sides of the sensor's longitudinal axis. Additionally, the frame 52 comprises recesses 62, on each side edge at the rearward end thereof. The recesses 62 and tabs 60 are disposed to engage the projections 29, 49 and recesses 27, 47, respectively, of the top and bottom members 10, 30. In this regard, it is noted that the side edge surfaces adjacent to recesses 62 may be ramped to facilitate contact advancement relative to the projections 29, 49 during snap-fit engagement therebetween. As will be appreciated, removal/retraction of the projections 29, 49 and tabs 62 is restrained by the rims of recesses 62 and 27, 47, respectively, in two-dimensions after assembly. Once snapped into position, the cushion assemblies 50 are restricted from sliding longitudinally or laterally, or depthwise, relative to the interconnected top and bottom members 10, 30. Such interconnection further facilitates reliable retention of the stand-off end 101a by top member 10 and the top cushion assembly frame 52.

As may be appreciated, the emitter(s) 104 and detector(s) 106 may be mounted directly adjacent to the optical windows 56 which are supported by the pliable members 54. Therefore, upon any movement of a cushion assembly 50 relative to the top or bottom members 10, 30, the interconnected emitters(s) 104 or detector(s) 106 will correspondingly move therewith.

Referring now FIGS. 1 and 2, assembly of the sensor embodiment will be briefly described. Initially, emitter(s) 104 and detector(s) 106 may be secured adjacent to the optical window 56 of their corresponding cushion assembly 50 (e.g., via adhesive or snap-fit interconnection). Further, a portion of stand-off end 101a may be located within and pulled-back relative to top member 10, wherein the stand-off end 101a is securely received in the opening 22.

To connect cushion assembly 50 to top member 10, the cushion assembly 50 is held at an angle relative to the top member 10, wherein the forward ends of each piece are immediately adjacent. The extending projections 60 on the forward edge of the frame 50 are then inserted into the recesses 27 in the forward end flange 20 of the top member 10. The wires 106 connected to emitter(s) 104 are then routed through notch 53 of the pliable member 54. Next, the rearward end of the cushion assembly 50 may be advanced toward the top member 10, wherein fins 26 will function to locate the frame 52. If properly aligned, the cushion assembly frame recesses 62 will engage the top member projections 29. A compressive force is then applied to force the cushion assembly 50 and top member 10 together. The top member 10 and cushion assembly 50 will 'snap-fit' together so that the top member projections 29 are restrainably engaged within the cushion assembly frame recesses 62. Assembly of the bottom member 30 and its corresponding cushion assembly 50 is substantially the same as the top member 10/cushion 50 assembly.

At this point, the top assembly of top member 10/cushion assembly 50 and the bottom assembly of bottom member 30/cushion assembly 50 are ready to be interconnected. For such purposes, the spring member 80 is oriented so that the wings 88, 90 point to the rearward end of the sensor assembly. The wiring 106 is then seated in the rearward extreme of the pass-through slot 92 and the hinge pin 100 is inserted through the opening 82 until the ends of the hinge pin 100 are flush with the side edges of the spring member 80. The hinge pin 110 is inserted from a proper end of the opening 82 so that the hinge pin key 114 is aligned with the hinge opening keyway 98. Insertion of the hinge pin 100 through the hinge opening 82 traps the wiring 106 in the pass through slot 92 behind the pin 110, thus isolating and protecting the wires.

Next, the spring member 80 may be located relative to the bottom member 30 so that the bottom wing 90 fits flushly within the rimmed rearward end 34 of the bottom member 30 and the bottom member stirrups 48 are located in correspondingly shaped seats on each side of the spring member 80. In this position, the opening 92 of spring member 80 should be aligned with the openings 32 in bottom member 30. Then, the top member 10 may be oriented such that the top and bottom cushions 50 are directly opposed along their longitudinal axes. The top member stirrups 28 may then be advanced and located adjacent to the outer-facing surfaces of the bottom member stirrups 48. Concomitantly, the spring member wing 88 may be flushly fitted in the rimmed rearward portion 14 of the top member 10. At this point, the bottom and top member opening 12, 32 and cylindrical hinge pin 110 are aligned. As such, hinge buttons 102 may be inserted from both sides and advanced until they are securely seated, thereby hingedly interconnecting the top and bottom members 10, 30, and completing the basic assembly procedure.

The embodiment described above is for exemplary purposes only and is not intended to limit the scope of the present invention. Various adaptations, modifications and extensions of the described system/method will be apparent to those skilled in the art and are intended to be within the scope of the invention as defined by the claims which follow.

What is claimed is:

1. A pulse oximetry sensor, comprising:

top and bottom members disposed in opposing and hinged relation;

at least one cushion for engaging a patient appendage; and, a plurality of interconnecting member sets for interconnecting said at least one cushion to one of said top and bottom members, wherein at least two of said interconnecting member sets are located on different sides of said at least one cushion to define corresponding transverse connection axes and combinatively restrict movement of said at least one cushion relative to said one of the top and bottom members in three dimensions.

2. The sensor of claim 1, wherein each of said interconnecting member sets comprises a projection and a mating recess.

3. The sensor of claim 2, wherein said at least one cushion comprises at least one said projection of a first set of said interconnecting member sets and at least one said mating recess of a second set of said interconnecting member sets.

4. The sensor of claim 2, wherein each said mating recess is configured to restrict movement of the corresponding projection in at least two dimensions.

5. The sensor of claim 4, wherein a first interconnecting member set is located to interconnect a first side of said at least one cushion to said one of said top and bottom members, and wherein a second interconnecting member set is located to interconnect a second side of said at least one cushion to said one of said top and bottom members.

6. The sensor of claim 5, wherein said first interconnecting member set is located so that upon interconnection the projection and recess of said second interconnecting member set are aligned for interconnection.

7. The sensor of claim 2, wherein the projection of at least one of said interconnecting member sets is of a wedge-shaped configuration.

8. The sensor of claim 1, wherein said at least one cushion comprises:
 a frame;
 a pliable member supported about a polygonal area by said frame; and
 an optical window supported about its periphery within said polygonal area by said pliable member.

9. The sensor of claim 8, wherein said pliable member is free to flex relative to said frame and thereby dispose said optical window in conformal, adjacent relation to a patient appendage.

10. The sensor of claim 9, further comprising:
 at least one of a light emitter and a light detector supportably interconnected to said optical window.

11. The sensor of claim 8, wherein said frame and said pliable member are configured to define a concave surface having a center axis extending parallel to a longitudinal center axis of the sensor.

12. The sensor of claim 8, wherein said pliable member comprises an elastomeric material over-molded onto said frame.

13. The sensor of claim 12, wherein said elastomeric material is a polymer.

14. The sensor of claim 12, wherein said frame is of a molded polymer construction.

15. The sensor of claim 12, wherein said pliable member is over-molded onto said optics window.

16. The sensor of claim 12, wherein said elastomeric material provides a tactile surface.

17. The sensor of claim 8, wherein each of said interconnecting member sets comprises a projection and a mating recess, and wherein said frame comprises at least one said projection of a first set of said interconnecting sets and at least one said mating recess of a second set of said interconnecting member sets.

18. The sensor of claim 17, wherein a first set of said interconnecting member sets are located on a front side of said frame and second and third sets of said interconnecting member sets are located on two opposing sides of said frame.

19. A pulse oximetry sensor, comprising:
 top and bottom members disposed in opposing relation; and,
 at least one cushion, interconnected to one of said top and bottom members, for engaging a patient appendage, including:
  a rigid frame defining an open area; and,
  a pliable member supportably over-molded on said rigid frame and extending across said open area, wherein said pliable member is free to flexibly deform across said open area relative to said frame.

20. The sensor of claim 19, wherein said at least one cushion further comprises:
 an optical window supported about its periphery within said open area by said pliable member, wherein said pliable member is free to flex relative to said frame and thereby dispose said optical window in conformal, adjacent relation to a patient appendage.

21. The sensor of claim 20, further comprising:
 at least one of a light emitter and a light detector supportably interconnected to said optical window.

22. The sensor of claim 14, further comprising:
 snap-fit means for interconnecting said at least one cushion to said one of said top and bottom members.

23. The sensor of claim 19, wherein said pliable member defines a tactile surface.

24. The sensor of claim 19, wherein said pliable member defines a semicylindrical surface for receiving a patient appendage.

25. The sensor of claim 19, wherein said pliable member comprises an elastomeric material.

26. A pulse oximetry sensor, comprising:
 top and bottom members disposed in opposing and hinged relation;
 top and bottom cushions interconnected to said top and bottom members, respectively, each of said cushions comprising:
  a frame defining an open area;
  a pliable member supportably interconnected to said rigid frame and extending across said open area, wherein said pliable member is free to flexibly deform across said open area relative to said frame;
  an optics window supported about its periphery by said pliable member within said open area; and,
 top and bottom snap-fit means for interconnecting said top cushion to said top member and for interconnecting said bottom cushion to said bottom member, respectively, wherein each of said top and bottom snap-fit means includes at least two interconnecting member sets that define corresponding connection axes which are transverse to one another.

27. The sensor of claim 26, further comprising:
 at least one of a light emitter and a light detector supportably interconnected to said optical window.

28. The sensor of claim 26, wherein said at least two interconnecting member sets combinatively restrict movement of each said cushion relative to each said top and bottom member in three dimensions.

* * * * *